(12) United States Patent
Tsai et al.

(10) Patent No.: US 11,175,519 B2
(45) Date of Patent: Nov. 16, 2021

(54) STRUCTURE OF GOGGLES

(71) Applicant: Broad Perspect Biomedical Technology Co., Ltd., New Taipei (TW)

(72) Inventors: Tsang-Chou Tsai, New Taipei (TW); John Huang, New Taipei (TW)

(73) Assignee: BROAD PERSPECT BIOMEDICAL TECHNOLOGY CO., LTD., New Taipei (TW)

( * ) Notice: Subject to any disclaimer, the term of this patent is extended or adjusted under 35 U.S.C. 154(b) by 261 days.

(21) Appl. No.: 16/653,952

(22) Filed: Oct. 15, 2019

(65) Prior Publication Data
US 2021/0109380 A1     Apr. 15, 2021

(51) Int. Cl.
| G02C 1/00 | (2006.01) |
| G02C 11/00 | (2006.01) |
| A61F 9/02 | (2006.01) |
| G02C 11/04 | (2006.01) |

(52) U.S. Cl.
CPC .............. *G02C 11/10* (2013.01); *A61F 9/026* (2013.01); *A61F 9/027* (2013.01); *G02C 11/04* (2013.01); *A61F 9/029* (2013.01); *G02C 1/00* (2013.01)

(58) Field of Classification Search
CPC .......... G02C 1/00; G02C 11/10; G02C 11/04; A61F 9/027; A61F 9/026; A61F 9/029; A61F 9/0079; A61F 9/00; A61F 9/02; A61F 9/04; A61F 9/06
USPC ........ 351/158, 41, 111, 121; 606/1, 4; 607/1
See application file for complete search history.

(56) References Cited

U.S. PATENT DOCUMENTS

2018/0224674 A1*  8/2018  Carabin ................... A61C 5/00

\* cited by examiner

*Primary Examiner* — Hung X Dang
(74) *Attorney, Agent, or Firm* — Leong C. Lei

(57) ABSTRACT

A structure includes a goggles body including rim sections and temple sections, an imaging device arranged between the rim sections, light-emitting elements arranged on an outer edge of the rim sections, and an electricity supply element, a control module, a storage device, and a data transmission device arranged in the temple sections. A server host device is also included. The server host device includes a wireless transmission module, a recognition processing module, and a driving processing element. As such, a surgeon may wear the goggles body in a surgical operation to acquire supplemented lighting in the eyesight range and a function of recording the entire process of the surgical operation. The surgeon may take a motion of a predetermined hand gesture to issue a control instruction corresponding thereto in order to execute the control instruction on a medical device to allow the surgeon to control hardware necessary for the operation.

10 Claims, 10 Drawing Sheets

STRUCTURE OF GOGGLES

TECHNICAL FIELD OF THE INVENTION

The present invention relates to a structure of goggles that enables combination of functions, such as light supplementing for eyesight, surgical recording, and hand gesture controlling external medical equipment, with a goggles body.

DESCRIPTION OF THE PRIOR ART

Due to an available space in an operation platform being limited, during the process of a surgical operation, it often lacks an instant control and recording system that operates at a direct viewing angle of a primary operation person. And, this leads to significant drawbacks having a blind area and losing or missing necessary records in case that replaying may not be available for technical instruction and operation skill viewed at the direct viewing angle. Further, during the process of a surgical operation, lighting is of significant importance; however, regular lighting for surgical operation rooms is generally supplied from one or more operating lamps, such that even such operating lamps provide sufficient luminance, lighting is often set at an imperfect angle. Although adjusting can be made by medical assistants, such an adjustment may not be timely and proper.

Mounting a recording device or a lighting device on goggles is known. However, such a device inevitably adds an extra weight, and would cause a burden to an operating person when mounted to the goggles. In addition, equipment that is necessarily controlled and operated by the primary operating person includes various devices, such as a pneumatic device, other than just recording and lighting devices. Goggles that are conventionally provided for use in operating rooms do not provide the primary operating person with an environment of easy operation.

SUMMARY OF THE INVENTION

The primary objective of the present invention is that an imaging device and a lighting element are additionally mounted to a body of surgical goggles to enhance brightness in the eyesight range of an operator and to provide a function of recording of the entire process of a surgical operation, and to additionally provide a function of using a hand gesture to control external medical equipment through collaborative operation of the imaging device with a data transmission device and a recognition processing module.

The present invention has a main structure that includes: a goggles body, which comprises two rim sections, a connection section formed between the rim sections, and two temple sections coupled to two opposite ends of the rim sections, wherein the temple sections are provided therein with at least one electricity supply element and a control module in electrical connection with the electricity supply element. The connection section is provided thereon with at least one imaging device in electrical connection with the control module for recording a surgical operation and capture an image of a movement of a hand gesture. A plurality of light-emitting elements are provided on an outer edge of each of the rim sections and are in electrical connection with the control module. The temple sections are provided therein with at least one storage device in electrical connection with the imaging device and a data transmission device in information connection with the imaging device. A server host device is also included, wherein the server host device is provided therein with a wireless transmission module in wireless connection with the data transmission device, a recognition processing module arranged in the server host device and in electrical connection with the wireless transmission module, and a driving processing element arranged in the server host device and in electrical connection with the recognition processing module. As such, the recognition processing module is operable to recognize the image of the movement of the hand gesture to generate a control instruction, so that the driving processing element is operated to execute the control instruction on a medical device.

To use, the goggles body are worn to be located in front of eyes or eyeglasses and the electricity supply element supplies electricity to the imaging device and the light-emitting elements. Since the imaging device and the light-emitting elements are arranged to face the same direction as the sight lines of the user, supplementing of light to the viewing range of the user can be achieved, and a function of recording of the entire process of a surgical operation at a first person view angle can be provided. Further, when the user makes an operation of taking a predetermined movement of a hand gesture in front of the imaging device, the data transmission device instantaneously transmit an image of the movement of the hand gesture to the server host device, so that the recognition processing module may be operated to recognize the image of the movement of the hand gesture to generate a control instruction, and subsequently executing the control instruction on a medical device by means of a driving processing element, in order to provide the user with more controllability and conveniences of the medical device during the process of a surgical operation.

DETAILED DESCRIPTION OF THE PREFERRED EMBODIMENT

Figure 1:
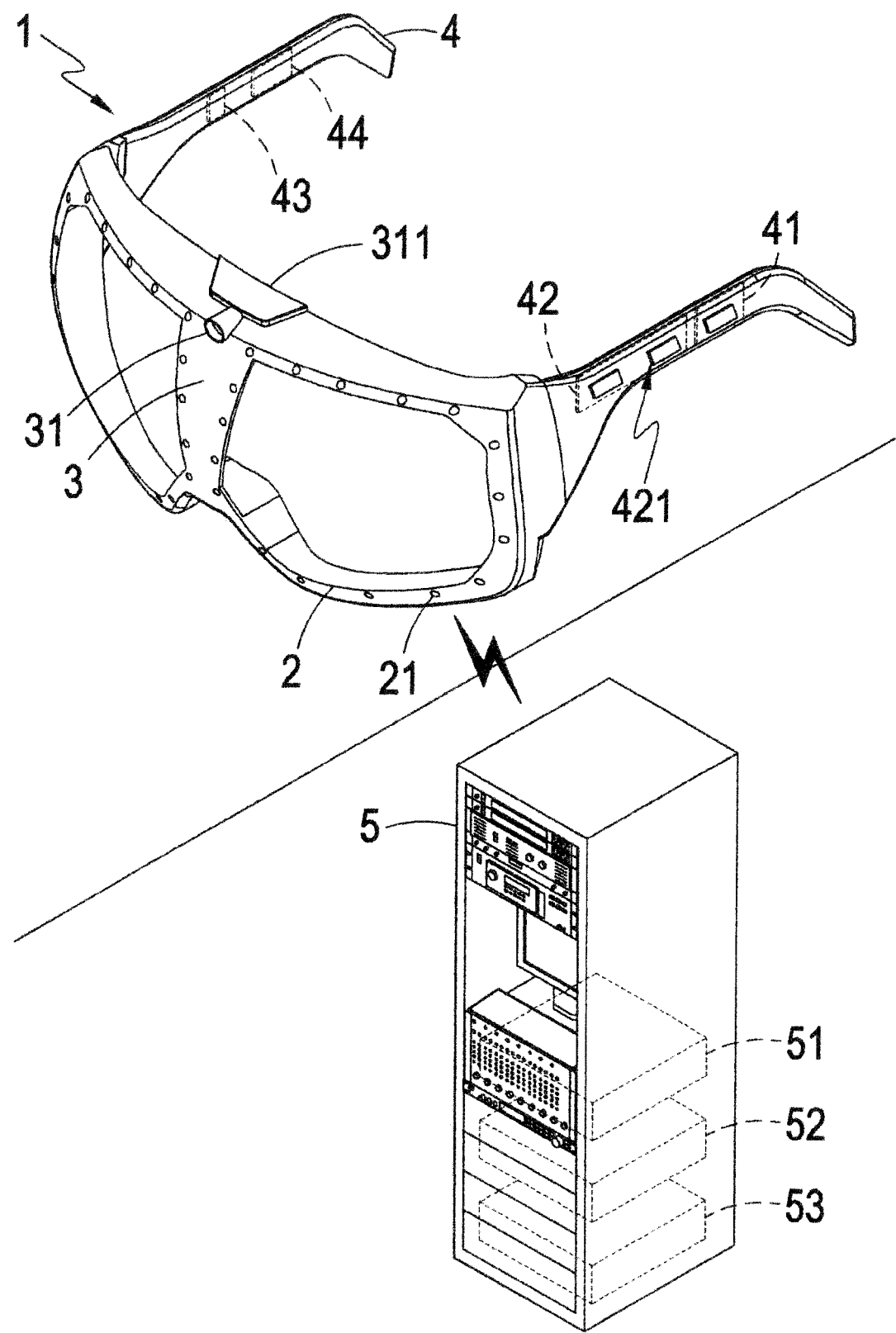
FIG. 1 is a perspective view of the present invention.
Figure 2:
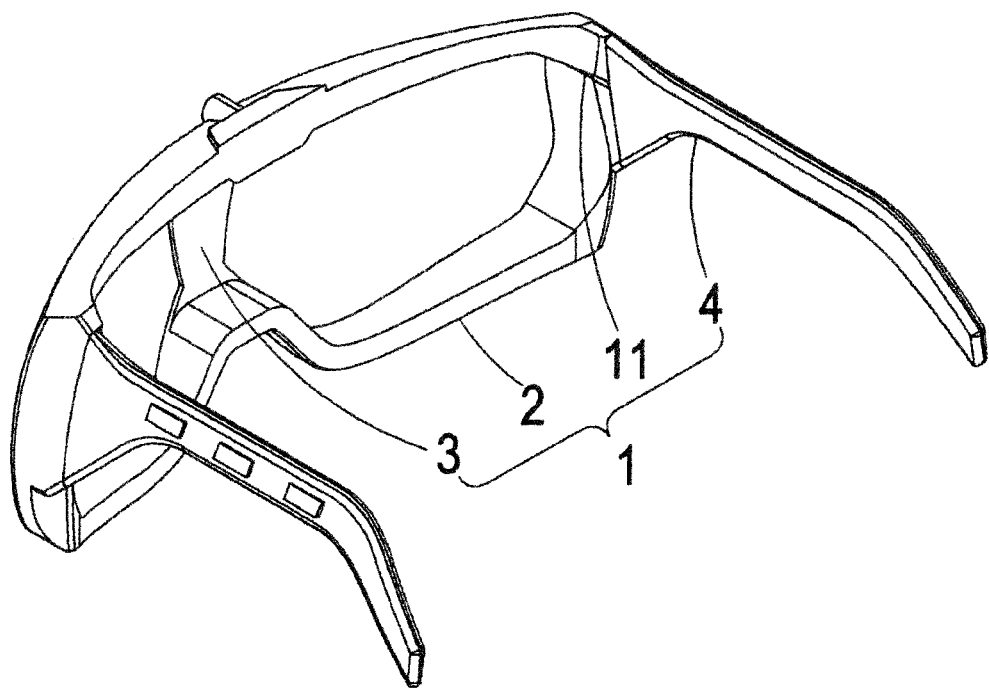
FIG. 2 is a perspective view, taken from a different angle, showing a goggles body according to the present invention.
Figure 3:
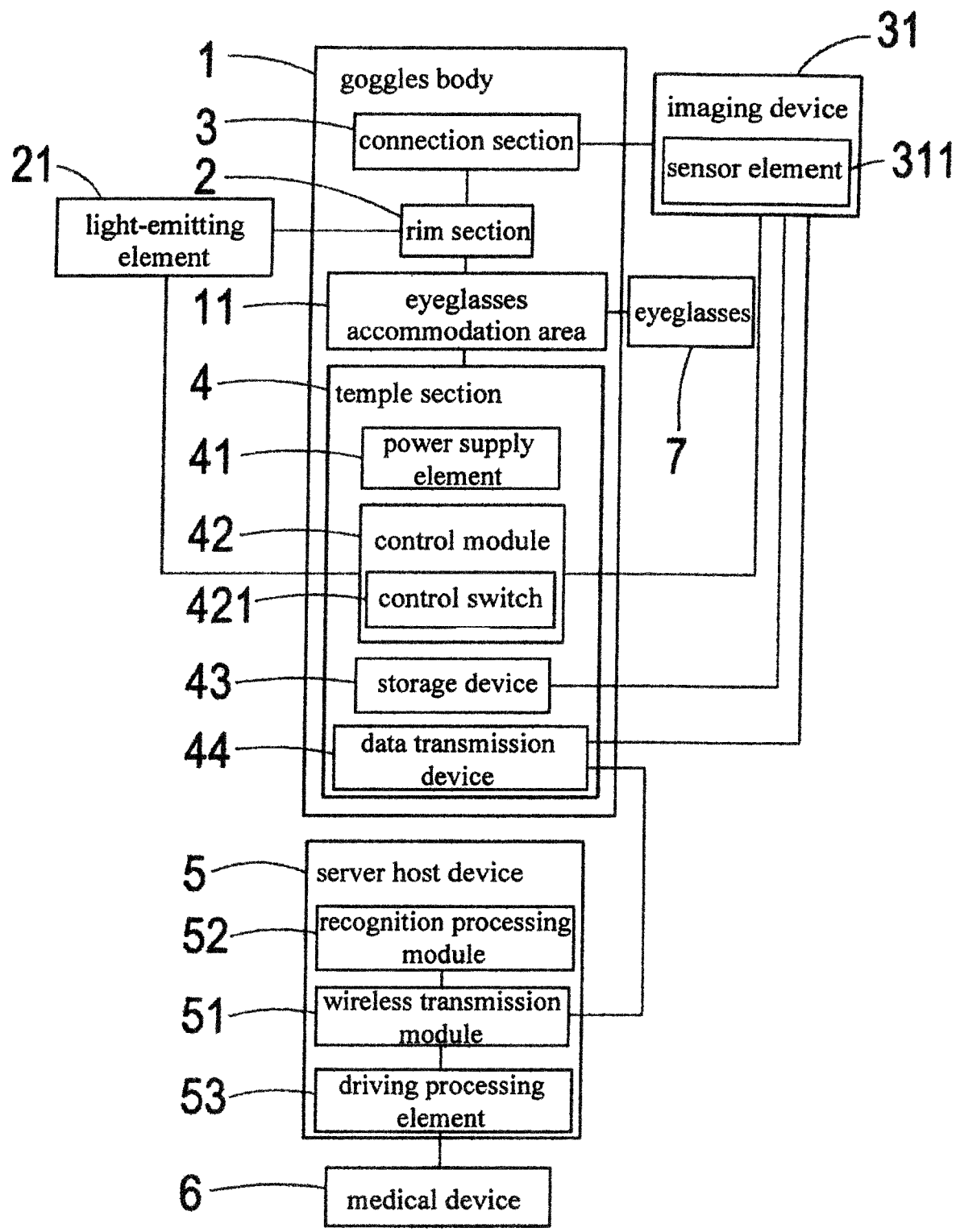
FIG. 3 is a block diagram of the present invention.

As shown in FIGS. 1-3, the present invention comprises:

a goggles body 1, which comprises two rim sections 2, a connection section 3 formed between the rim sections 2, and two temple sections 4 coupled to two opposite ends of the rim sections 2, wherein an eyeglasses accommodation area 11 is defined between the rim sections 2 and one side of each of the temple sections 4 for receiving therein eyeglasses temples of eyeglasses 7;

at least one electricity supply element 41 that is arranged in the temple sections 4;

a control module 42 that is arranged in the temple sections 4 and is in electrical connection with the electricity supply element 41;

at least one control switch 421 that is arranged on the temple sections 4 and is in electrical connection with the control module 42;

at least one imaging device 31 that is arranged on the connection section 3 and is in electrical connection with the control module 42 and is operable for recording a surgical operation and capture an image of a movement of a hand gesture, wherein the image-taking device 31 is provided thereon with a sensor element 311, which is operable to detect the movement of the hand gesture to drive the imaging device 31 to carry out an operation of capturing the image of the movement of the hand gesture;

a plurality of light-emitting elements 21 that are arranged on an outer circumferential edge of each of the rim sections 2 and are in electrical connection with the control module 42;

at least one storage device 43 that is arranged in the temple sections 4 and is in electrical connection with the imaging device 31;

a data transmission device 44 that is arranged in the temple sections 4 and is in information connection with the imaging device 31, wherein the electricity supply element 41, the control module 42, the storage device 43, and the data transmission device 44 are arranged to achieve uniform weight distribution on the temple sections 4 in combination with or taking into consideration of weights of the imaging device 31 and the light-emitting elements 21; and a server host device 5, wherein the server host device 5 is provided therein with a wireless transmission module 51 (such as a network card) that is in wireless connection with the data transmission device 44, a recognition processing module 52 that is arranged in the server host device 5 and is in electrical connection with the wireless transmission module 51, and a driving processing element 53 that is arranged in the server host device 5 and is in electrical connection with the recognition processing module 52, wherein the recognition processing module 52 is operable to recognize the image of the movement of the hand gesture to generate a control instruction, so that the driving processing element 53 is operated to execute the control instruction on a medical device 6.

Figure 4:
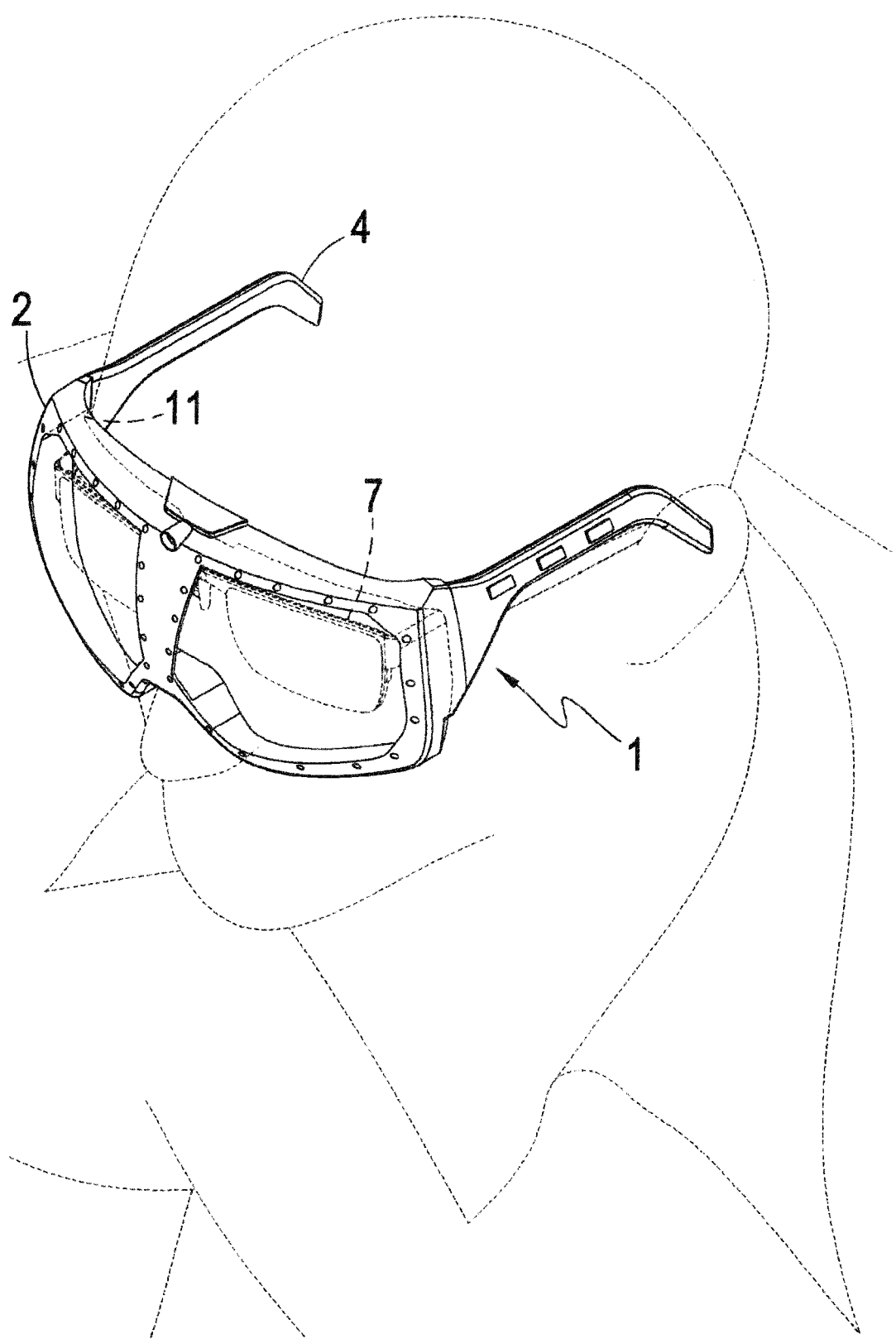
FIG. 4 is a schematic view showing the present invention being worn.

As shown in FIGS. 1-8, the goggles body 1 of the present invention uses the eyeglasses accommodation area 11 that is formed between the rim sections 2 and one side of each of the temple sections 4 to receive and hold the eyeglasses 7 of a user therein and the main purpose is to allow the user who wears a pair of eyeglasses 7 already to directly put on the goggles body 1 without the need to consider the diopter of the lenses. As such, the eyeglasses accommodation area 11 is provided for receiving and holding the eyeglasses temples of the eyeglasses 7 and to allow the goggles body 1 to cover, attach to, or enclose the eyeglasses 7, providing the user with comfortable feeling of wearing (as shown in FIG. 4).

Figure 5:
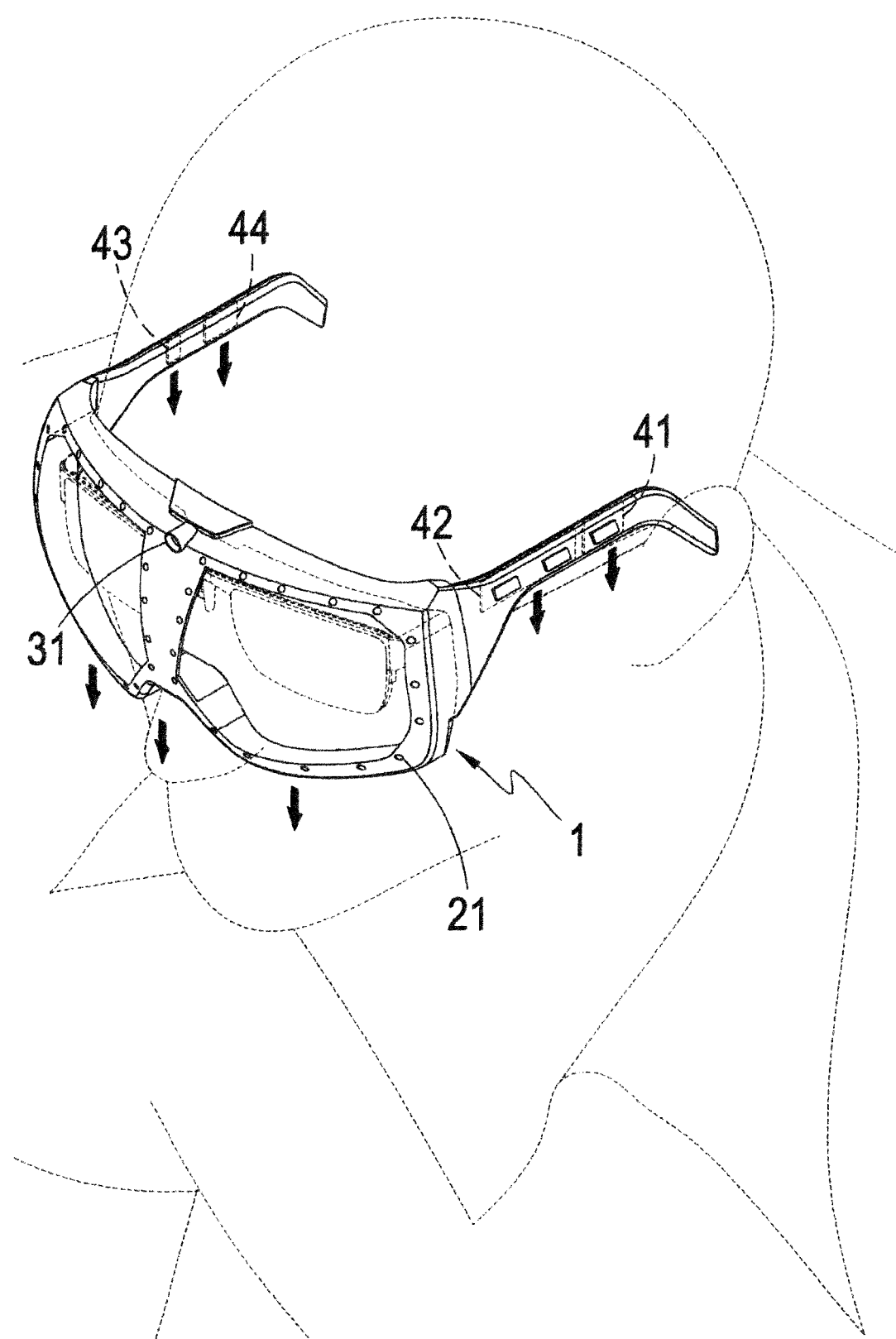
FIG. 5 is a schematic view showing weight distribution of the present invention.

As shown in FIG. 5, the goggles body 1 of the present invention is generally used in a surgical operation scenario and it is often worn for an extended period of time when used. As such, in addition to conformable feeling mentioned above, weight balance is also a significant issue in the use of the goggles body 1. Thus, the imaging device 31 that must be set up to match the eyesight of the user is arranged on the connection section 3 that is located in-between the two eyes of the user and the light-emitting elements 21 (such as light-emitting diodes, LEDs) that must be set up according to the eyesight field of the user are arranged circumferentially along the outer edges of the rim sections 2, and the remaining parts or devices or structures, which include the electricity supply element 41 (such as an electric cell), the control module 42 (such as a circuit substrate), the storage device 43 (such as a memory card), and the data transmission device 44 (such as a WIFI router), are arranged, in a uniform weight distribution manner, on the two temple sections 4. This is different from the prior art arrangement, in which all such devices are arranged at a front side of goggles, by uniformly distributing the weights on the rim sections 2 and the temple sections 4 of the goggles body 1, such that the total weight of the goggles body 1 are collaboratively supported by the nose and the ears of the user and the loading applied to the user is uniform and the burden of the user could be reduced to thereby allow for an even much more extended period of time for wearing.

Figure 6:
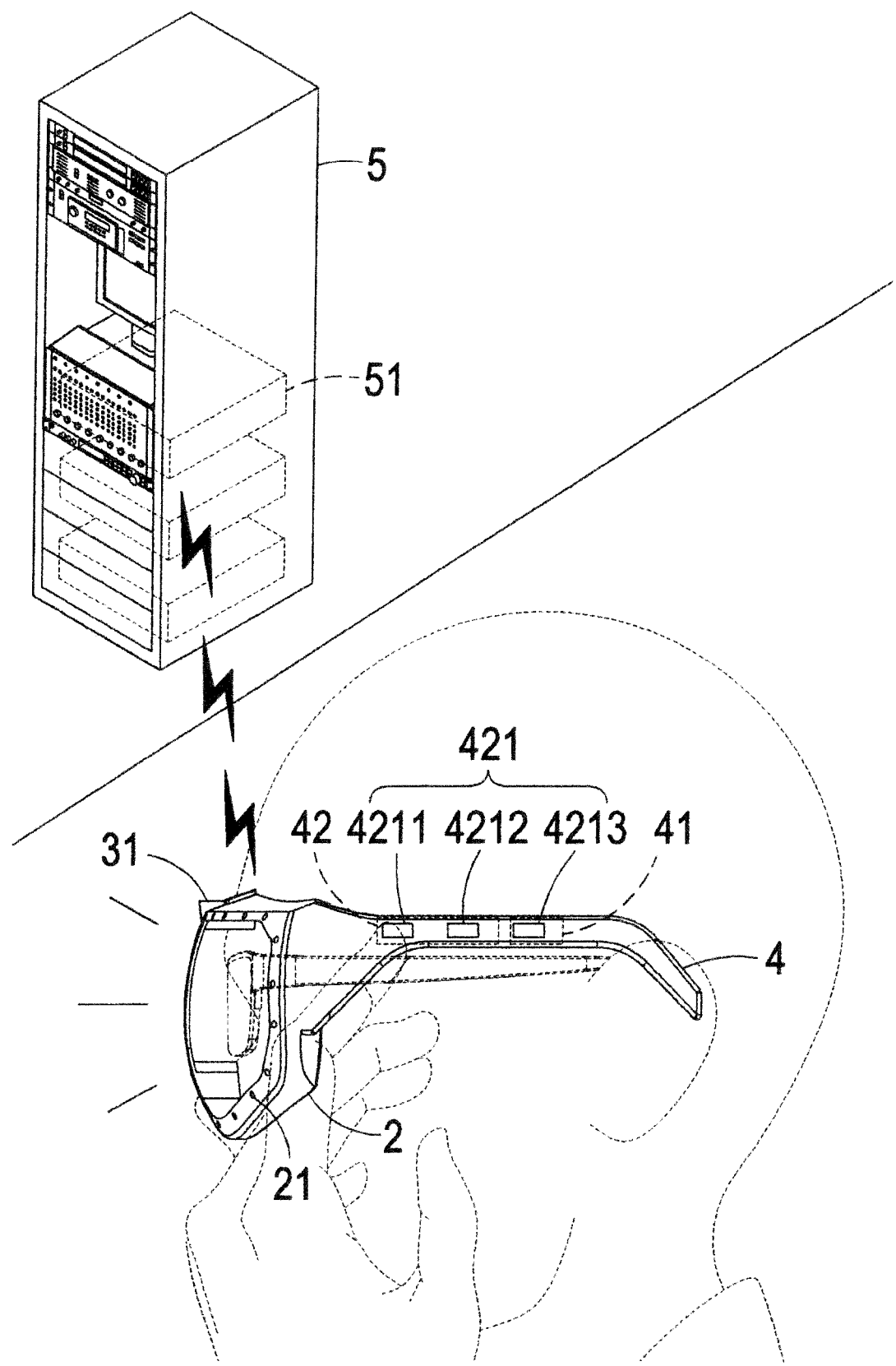
FIG. 6 is a schematic view illustrating use of the present invention.

In practical use, the user may operate the control switch 421 that is provided on the temple sections 4 to drive or actuate the control module 42, such as pressing down the power switch 4211 of the control switch 421 to cause the electricity supply element 41 to turn on the light-emitting elements 21 and the imaging device 31 and allowing the electricity supply element 41 to supply electrical power to the light-emitting elements 21 for emission of light and also allowing the electricity supply element 41 to supply electrical power to the imaging device 31 for activation of image taking or video recording. In case of requiring no lighting, a light switch 4212 of the control switch 421 can be pressed down to turn off lighting of the light-emitting elements 21; or in case of requiring no video recording or image taking, a recording switch 4213 of the control switch 421 can be pressed down to turn off an image taking operation or a video recording operation of the imaging device 31. It is noted that since the light-emitting elements 21 are arranged along outer circumferential edges of the rim sections 2, the area that is covered by the eyesight of the user can be supplied with sufficient lighting from the light-emitting elements 21; and the imaging device 31 is arranged on the connection section 3 and is operable to make video recording or image taking at a first person view angle of the user for the entire process of a surgical operation (as shown in FIG. 6); and the image taken by or the video recorded by the imaging device 31 is directly stored in the storage device 43 to serve as a complete record of the surgical operation and also, an operation of the data transmission device 44 that is in wireless connection with the wireless transmission module 51 can transmit the image or video to the server host device 5 for synchronous displaying to be watched by other persons as a measure for facilitating collaborative consultation or instructive training for major surgical operations. This helps reduces the number of persons staying in the operating room and would be helpful in reducing the risk of infection.

Figure 7:
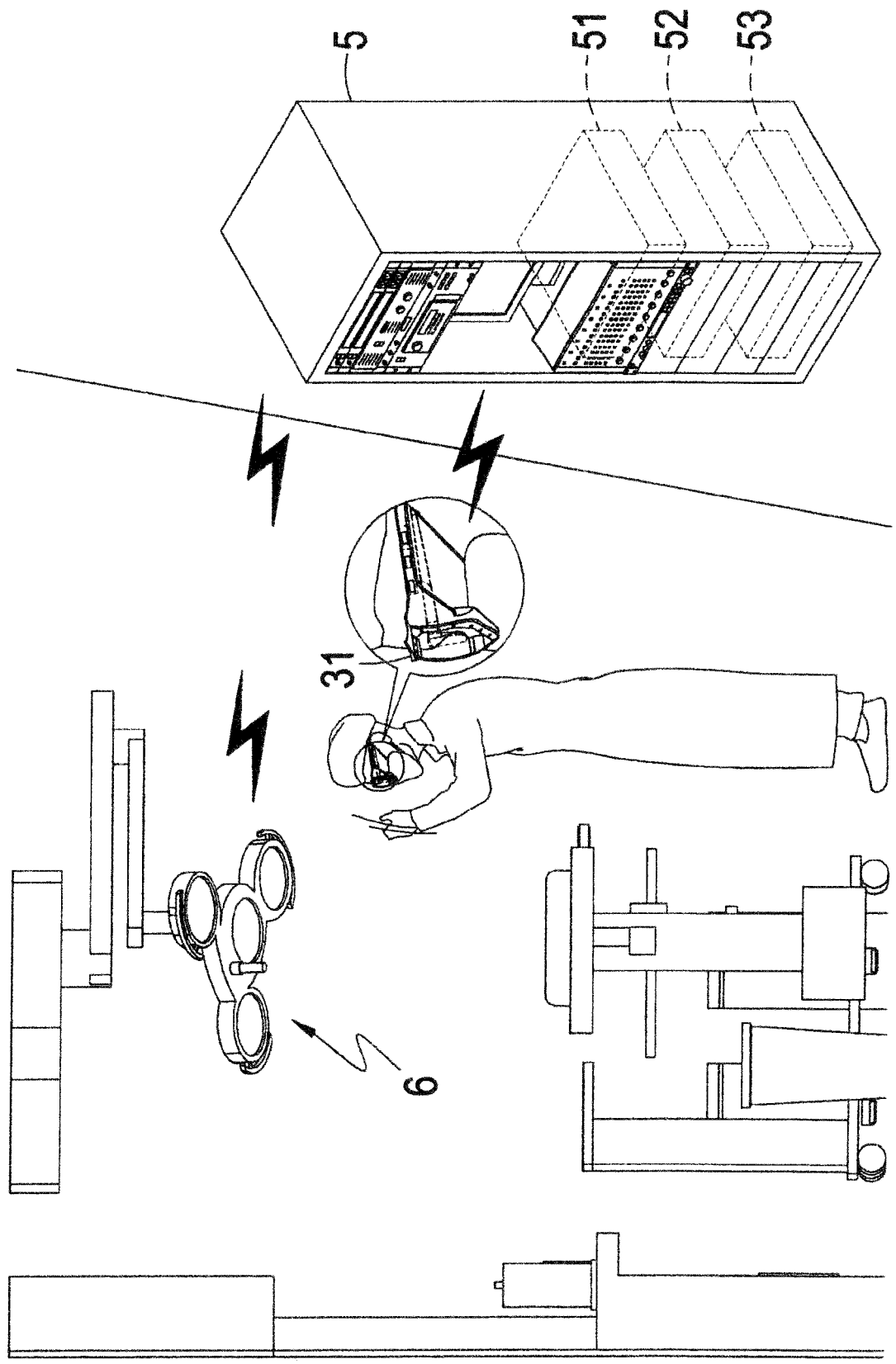
FIG. 7 is a schematic view illustrating hand gesture controlling according to the present invention.
Figure 8:
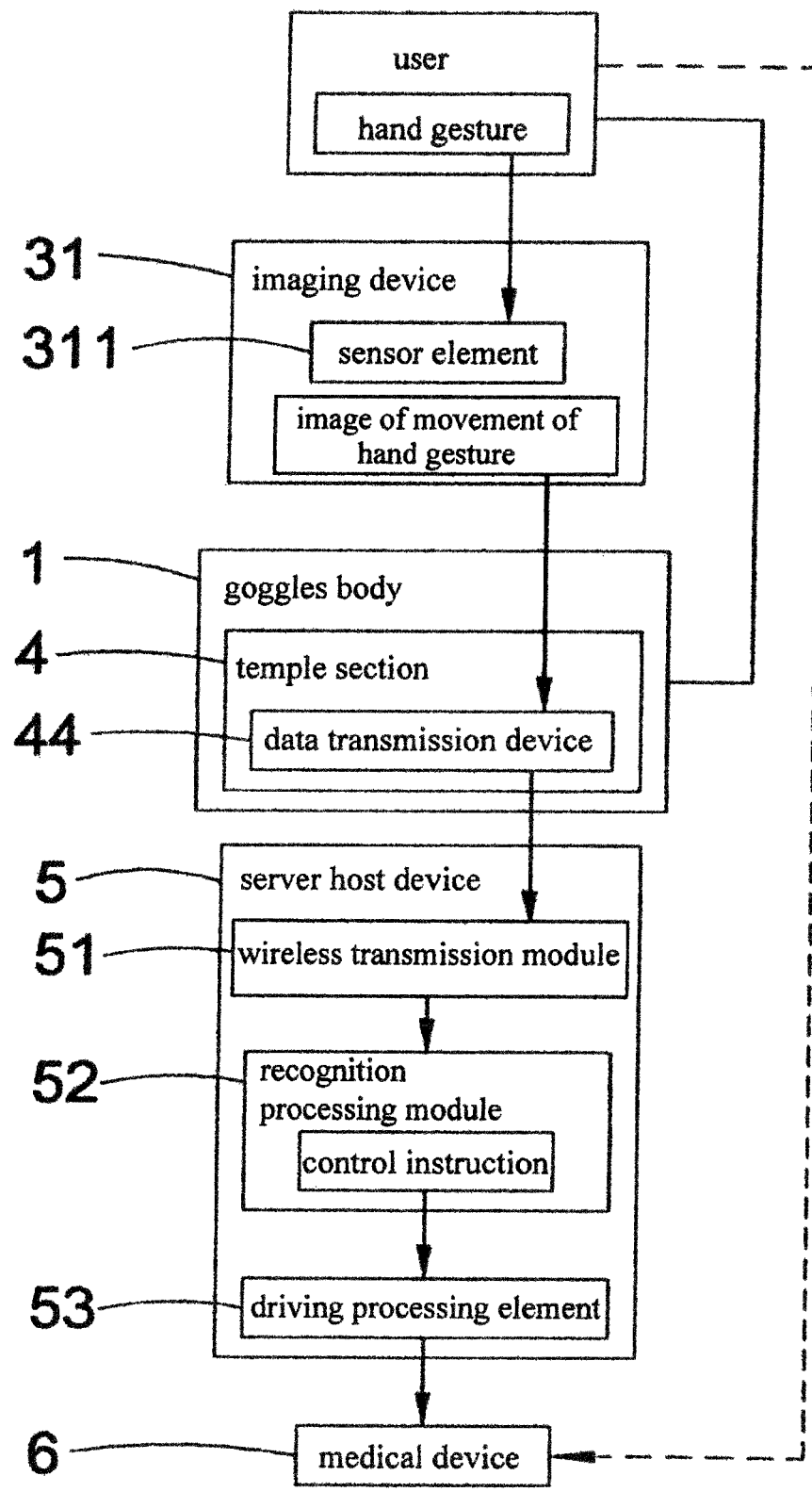
FIG. 8 is flow chart illustrating a hand gesture controlling process.

As shown in FIGS. 7-8, when the sensor element 311 detects the movement of a hand gesture, the imaging device 31 is activated to capture an image of the movement of the hand gesture of a user, and the image of the movement of the hand gesture is transmitted through the data transmission device 44 that is in wireless connection with the wireless transmission module 51 to the server host device 5, and the recognition processing module 52 may compare the image of the movement of the hand gesture to a database, such that when the comparison matches, the recognition processing module 52 generates a control instruction, and the driving processing element 53 is operated to execute the control instruction on a medical device 6. For the user, such a function is equivalent to using the movement of the hand gesture to issue the control instruction, so that the user may have direct control of for example operating lamps and a pneumatic device based medical device 6 (the control operation being shown in phantom lines). As such, unnecessary misunderstanding between the user and an assistant can be reduced and timeliness and appropriateness of control and operation of the medical device 6 are enhanced. Such a hand gesture control technique can be implemented through a control program written by a technician and loaded in a chip (namely the recognition processing module 52). In this embodiment, the sensor element 311 being operable to activate or initiate the operation of capturing the image of the movement of a hand gesture is provided as an illustrative example, and this invention is not constrained to such an example.

Figure 9:
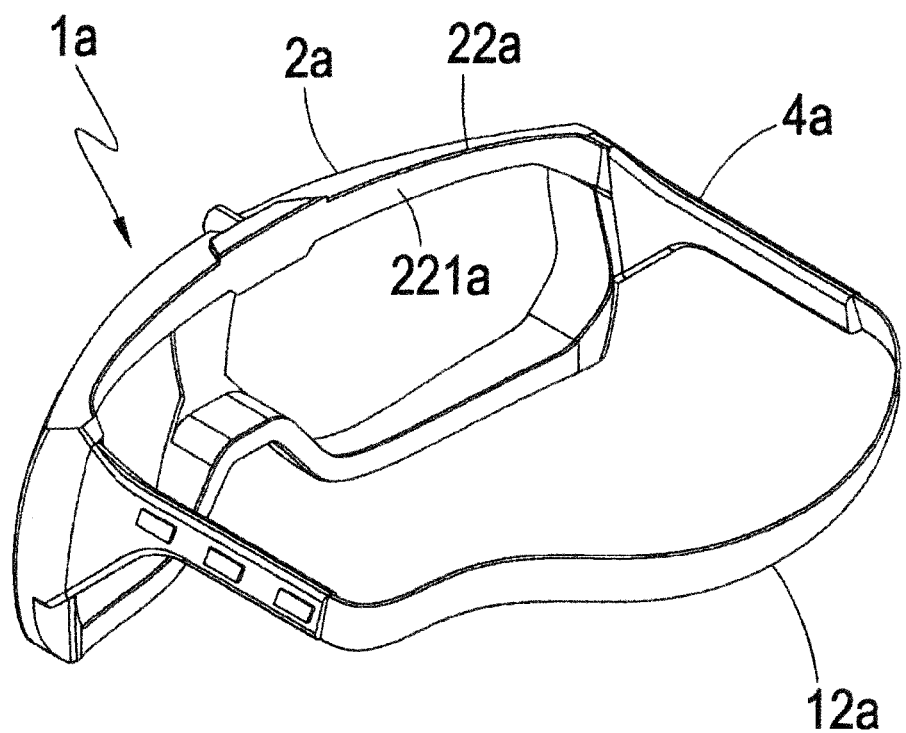
FIG. 9 is a perspective view showing a goggles body according to another embodiment of the present invention.

As shown in FIG. 9, in the instant embodiment, an elastic fastening strap 12*a* is provided at ends of the temple sections 4*a* that are distant from the rim sections 2*a*, and at least one flexible sealing pad 22*a* is provided on an inside edge of the rim sections 2*a*. The flexible sealing pad 22*a* is provided, on one side thereof, with an attachment curved surface 221*a* that is an ergonomic surface matching a contour of a face of a user. As such, the elastic fastening strap 12*a* can be used in such a way as being that for sports goggles to provide assisting support from the rear of the user's head, and in addition to enhancing stability of wearing the goggles body 1*a*, this also help spread the force applied to the nose and the ears to thereby reduce the burden of weight that the user needs to take. The flexible sealing pad 22*a* could be kept in tight engagement with the user's face so as to enhance comfortability of wearing for the user and also prevents sweat or other forging objects from invading. Further, the inside surface of the flexible sealing pad 22*a* is the attachment curved surface 221*a* that is designed ergonomically so as to reduce undesired pressurizing of the face by the flexible sealing pad 22*a*, while ensuring wearing comfortability of the user.

Figure 10:
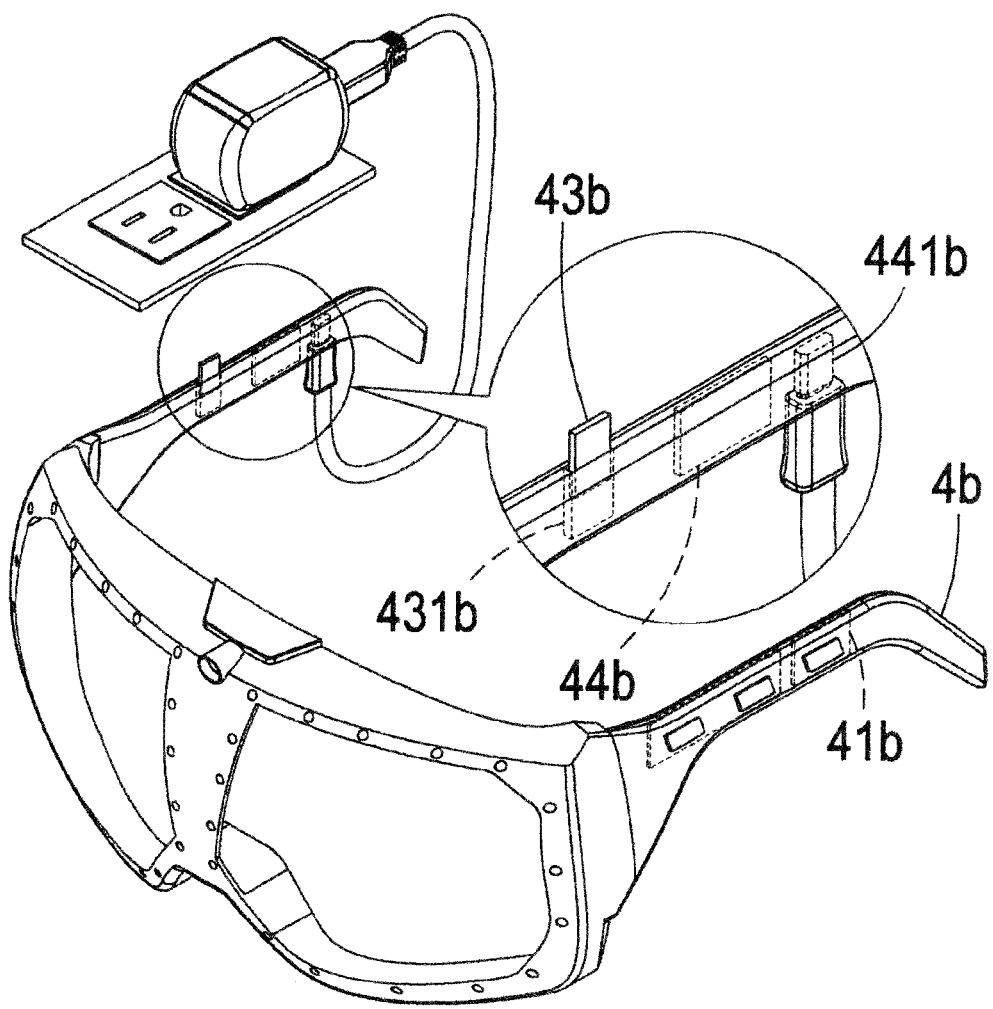
FIG. 10 is a schematic view illustrating use of another embodiment of the present invention.

As shown in FIG. 10, in the instant embodiment, the data transmission device 44*b* comprises a connection port 441*b* that is in electrical connection with the electricity supply element 41*b* and the storage device 43*b*. The temple sections 4*b* is provided thereon with a receiving slot 431*b* for receiving and retaining, in a removable manner, the storage device 43*b*. As such, a common and simple way of connection, through for example micro USB Type B coupling, to the connection port 441*b* allows for charging of the electricity supply element 41*b* or reading of images or video stored in the storage device 43*b*. The storage device 43*b* may alternatively be in the form of a memory card, and under such a condition, the storage device 43*b* can be directly withdrawn from the receiving slot 431*b* and a card reader may be used to access the images or video recorded and stored therein to provide the user with a simple and easy way of data transmission and electricity supply.

We claim:

1. A structure of goggles, mainly comprising:
    a goggles body, which comprises two rim sections, a connection section formed between the rim sections, and two temple sections coupled to two opposite ends of the rim sections;
    at least one electricity supply element that is arranged in the temple sections;
    a control module that is arranged in the temple sections and is in electrical connection with the electricity supply element;
    at least one imaging device that is arranged on the connection section and is in electrical connection with the control module and is operable for recording a surgical operation and capture an image of a movement of a hand gesture;
    a plurality of light-emitting elements that are arranged on an outer circumferential edge of each of the rim sections and are in electrical connection with the control module;
    at least one storage device that is arranged in the temple sections and is in electrical connection with the imaging device;
    a data transmission device that is arranged in the temple sections and is in information connection with the imaging device; and
    a server host device, wherein the server host device is provided therein with a wireless transmission module that is in wireless connection with the data transmission device, a recognition processing module that is arranged in the server host device and is in electrical connection with the wireless transmission module, and a driving processing element that is arranged in the server host device and is in electrical connection with the recognition processing module, wherein the recognition processing module is operable to recognize the image of the movement of the hand gesture to generate a control instruction, so that the driving processing element is operated to execute the control instruction on a medical device.

2. The structure of goggles according to claim 1, wherein the imaging device is provided thereon with a sensor element, which is operable to detect the movement of the hand gesture to drive the imaging device to carry out an operation of capturing the image of the movement of the hand gesture.

3. The structure of goggles according to claim 1, wherein an elastic fastening strap is provided at ends of the temple sections that are distant from the rim sections.

4. The structure of goggles according to claim 1, wherein the temple sections comprise a control switch mounted thereon and in electrical connection with the control module.

5. The structure of goggles according to claim 1, wherein the temple sections comprise a receiving slot form therein for removably receiving and retaining the storage device.

6. The structure of goggles according to claim 1, wherein the data transmission device comprises a connection port in electrical connection with the electricity supply element and the storage device.

7. The structure of goggles according to claim 1, wherein the rim sections have an inside edge that includes at least one flexible sealing pad mounted thereto.

8. The structure of goggles according to claim 7, wherein the flexible sealing pad has a side that includes a attachment curved surface, which is an ergonomic curved surface matching a contour of a human face.

9. The structure of goggles according to claim 1, wherein the goggles body comprises an eyeglasses accommodation area that is formed between the rim sections and a side of each of the temple sections adapted to receive templates of eyeglasses.

10. The structure of goggles according to claim 1, wherein the electricity supply element, the control module, the storage device, and the data transmission device are arranged to achieve uniform weight distribution on the temple sections in combination with weights of the imaging device and the light-emitting elements.

* * * * *